(12) United States Patent
Freund et al.

(10) Patent No.: US 10,737,230 B2
(45) Date of Patent: Aug. 11, 2020

(54) REACTOR AND METHOD FOR MAXIMIZING METHANOL YIELD BY USING CATALYST LAYERS

(71) Applicants: CLARIANT INTERNATIONAL LTD, Muttenz (CH); L'AIR LIQUIDE SOCIÉTÉ ANONYME POUR L'ETUDE ET L'EXPLOITATION DES PROCÉDÉS GEORGES CLAUDE, Paris (FR)

(72) Inventors: Hannsjoerg Freund, Baiersdorf (DE); Robert Frind, Kreischa (DE); Tobias Henkel, Louisville, KY (US); Markus Kaiser, Fuerth (DE); Timm Schuhmann, Offenbach (DE); Wolfgang Seuffert, Bruckmuehl (DE); Sebastian Werner, Vaterstetten (DE)

(73) Assignees: CLARIANT INTERNATIONAL LTD, Muttenz (CH); L'AIR LIQUIDE SOCIÉTÉ ANONYME POUR L'ETUDE ET L'EXPLOITATION DES PROCÉDÉS GEORGES CLAUDE, Paris (FR)

(*) Notice: Subject to any disclaimer, the term of this patent is extended or adjusted under 35 U.S.C. 154(b) by 0 days.

(21) Appl. No.: 16/485,848

(22) PCT Filed: Feb. 13, 2018

(86) PCT No.: PCT/EP2018/053518
§ 371 (c)(1),
(2) Date: Aug. 14, 2019

(87) PCT Pub. No.: WO2018/149811
PCT Pub. Date: Aug. 23, 2018

(65) Prior Publication Data
US 2020/0001261 A1    Jan. 2, 2020

(30) Foreign Application Priority Data

Feb. 15, 2017 (DE) .................... 10 2017 001 520

(51) Int. Cl.
*C07C 29/151* (2006.01)
*C07C 29/152* (2006.01)
(Continued)

(52) U.S. Cl.
CPC ........... B01J 8/0492 (2013.01); B01J 8/0496 (2013.01); C07C 29/151 (2013.01);
(Continued)

(58) Field of Classification Search
None
See application file for complete search history.

(56) References Cited

U.S. PATENT DOCUMENTS

2012/0322651 A1*  12/2012  Schlichting ............ B01J 8/0457
                                                          502/100
2018/0237366 A1*   8/2018  Modarresi ............ B01J 19/0013

FOREIGN PATENT DOCUMENTS

WO    WO 2009/082930 A1    7/2009
WO    WO 2011/101081 A1    8/2011

OTHER PUBLICATIONS

International Search Report and Written Opinion dated Apr. 12, 2018 issued in PCT/EP2018/053518.

\* cited by examiner

*Primary Examiner* — Medhanit W Bahta
(74) *Attorney, Agent, or Firm* — Scully, Scott, Murphy & Presser, P.C.

(57) ABSTRACT

The invention relates to a reactor for the catalytic production of methanol, in which at least two catalyst layers are arranged. The first catalyst layer is arranged upstream and
(Continued)

the second catalyst layer is arranged downstream. The activity of the first catalyst layer is higher than the activity of the second catalyst layer.

17 Claims, 5 Drawing Sheets

(51) Int. Cl.
*C07C 29/153* (2006.01)
*C07C 29/154* (2006.01)
*B01J 8/04* (2006.01)

(52) U.S. Cl.
CPC ........ *C07C 29/152* (2013.01); *C07C 29/1516* (2013.01); *B01J 2208/00106* (2013.01); *B01J 2208/025* (2013.01); *B01J 2208/027* (2013.01)

| 2 | empty |

| 1 | MM800 6x4 mm | C79-5 5x5 mm | MM800 6x4 mm | MM800 3x3 mm | |

Fig. 5

REACTOR AND METHOD FOR MAXIMIZING METHANOL YIELD BY USING CATALYST LAYERS

The present application is a '371 of International Application Number PCT/EP2018/053518, which was filed on Feb. 13, 2018, the contents of which are incorporated by reference.

The invention relates to a reactor for the catalytic production of methanol and a method for the catalytic production of methanol from synthesis gas.

Methods for the production of methanol by catalytic conversion of hydrogen and carbon oxides containing synthesis gas are known in the art for a long time. Ullmann's Encyclopedia of Industrial Chemistry, Sixth Edition, 1998 Electronic Release, chapter "Methanol", subchapter 5.2 "Synthesis" describes a single-step method for the production of methanol.

The known synthesis of methanol from carbon monoxide, carbon dioxide and hydrogen can be described by the following equations:

$$CO + 2H_2 \rightleftharpoons CH_3OH; \quad (1)$$

$$CO_2 + 3H_2 \rightleftharpoons CH_3OH + H_2O; \quad (2)$$

$$CO + H_2O \rightleftharpoons H_2 + CO_2 \quad (3)$$

These three equations are exothermic. In the reactions 1 and 2, methanol is produced. Low temperatures and a rise in pressure leads to a shift of the equilibrium towards the desired product methanol. The simultaneously occurring reaction 3, which is also exothermic, is the so-called "water-gas-shift" reaction, in which carbon monoxide is converted into carbon dioxide.

Due to the high exothermic nature of the methanol synthesis, a very good temperature control of the reactor is necessary to prevent overheating of the catalyst, which would lead to a premature deactivation due to a loss of active metal surface by coagulation of the metal crystallites, the so-called sintering. In addition to this thermic effect, it is further known from the prior art that metal/carrier-catalysts such as the copper-based methanol synthesis catalyst are prone to surface restructuring under the influence of carbon oxides, which leads to a loss of active metal surface by sintering and therefore to a loss of activity. An exemplary reference is the publication of Nihou et al., Journal de Chimie Physique et de Physico-Chimie Biologique (1988), 85(3), p. 441-448, in which it has been shown by EPMA-analysis that the surface of catalysts of the type $CuO/ZnO/Al_2O_3$ during conversion of carbon oxides with hydrogen under methanol synthesis conditions restructures dynamically. This restructuring is more pronounced at high carbon oxide partial pressures than at low carbon oxide partial pressures.

Current developments of catalysts for methanol synthesis aim at providing catalysts which have a high synthesis activity at low reaction temperatures. Project brochures for currently available catalysts for methanol synthesis refer to their increased synthesis activity at low temperatures; an example is the brochure "MK-121—High activity methanol synthesis catalyst" (Haldor Topsoe A/S), which is available on the Internet at http://www.topsoe.com/. The increased low-temperature activity is enabled by an enhanced dispersion of the copper on the catalyst surface. Developments of other catalyst manufacturers are aiming in the same direction; Clariant offers the methanol synthesis catalyst Mega-Max® 800 as a further development of the catalyst Mega-Max® 700, wherein the first-mentioned newly developed catalyst has a higher activity at low temperatures due to optimized copper dispersion (Nitrogen+Syngas 290, 11-12 (2007), 26-42).

Generally, metal/carrier-catalysts with high dispersion are more vulnerable for deactivation as a result of sintering. MonzOn et al. could show in Applied Catalysis A: General 248 (2003), 279-289 that the velocity of the dispersion decrease of precious metal/carrier-catalysts follows a kinetic approach of $$dD_r/dt = \Psi_D (D_r - D_{rr})^n$$

Wherein $D_r$ is the relative dispersion, which is defined by the relation $D_r = D/D_0$, in which $D$ is the absolute value of the dispersion at the time t and $D_o$ is the absolute value of the dispersion at the time zero. $D_{rr}$ is the limit of the relative dispersion for $t \to \infty$; $\Psi_D$ is the kinetic constant of the deactivation. n is the kinetic order of the deactivation reaction; The above-mentioned citation states that the kinetic order can be satisfactorily described for all of the published data in the literature for the deactivation kinetics of precious metal/carrier-catalysts due to sintering with n=1 to 2. From this follows that a quicker relative dispersion decrease is to be expected when using a precious metal/carrier-catalyst with high dispersion under otherwise identical conditions. A quicker dispersion decrease leads to a quicker loss in activity and consequently to a lower long-term stability of the catalyst.

In the case that a catalyst with high activity is used, it has been shown that in the initial area of the reactor bed a pronounced non-isothermal reaction zone forms with a pronounced hotspot. This hotspot has a temperature of 30° C. to 40° C. above the temperature of the coolant and thus above the other temperature in the reactor. By this hotspot, the efficiency of the catalyst in this area is diminished, exemplarily to only about 50%. Furthermore, the increased temperature leads to a faster deactivation of the catalyst material due to sintering. The deactivation of the catalyst in turn leads to a migration of the hotspot through the reactor, whereby the catalyst as a whole is subject to faster deactivation.

A two-step method for the production of methanol is exemplarily known from the application WO 2011/101081 A1. There, a stream of synthesis gas containing hydrogen and carbon oxides is converted in two reaction stages in a water-cooled methanol synthesis reactor followed by a gas-cooled methanol synthesis reactor. In both synthesis reactors typically the same copper-based methanol synthesis catalysts are used. However, in the first reactor, a catalyst is used which has a lower activity than the catalyst which is used in the second reactor. Hereby, a fast loss of activity of the catalyst used in the first reactor due to high temperatures is prevented. By using a catalyst with a relatively low activity in the first reactor, the conversion of synthesis gas can be increased, if the reactors are used for a longer time. Here, the effect described in the above cited work of Monzón et al. is utilized. In more detail, the relative dispersion does not drop below the limit $D_{rr}$ of the relative dispersion for very long operating periods with defined reaction conditions. This means that precious metal/carrier-catalysts which are in operation for a long time have a dispersion which is different from zero and thus a rest activity. This observed inverse correlation between dispersion and activity on the one hand and long-term stability on the other hand for precious metal/carrier-catalysts is applicable to copper-based catalysts for methanol synthesis.

Besides the thermally caused deactivation of the catalyst, there exists a problem with large amounts of heat being generated when using catalyst material with high activity and with, consequently, high conversion of synthesis gas. The increasing temperature leads, apart from the above described deactivation of the catalyst, to the reaction reaching the thermodynamic equilibrium. When reaching the thermodynamic equilibrium, no further conversion of the synthesis gas occurs. In the further pathway of the catalyst bed lower temperatures then prevail together with a declining amount of carbon oxides in the synthesis gas, since a part of the oxides has already been converted. The highly-active and expensive catalyst is under these conditions not optimal for the conversion of the synthesis gas.

It is the objective of the present invention to improve a method for the production of methanol and the reactors used therein, such that the above described disadvantages are avoided or at least reduced and the space-time-yield is increased.

According to a first aspect of the invention, a reactor is provided for the catalytic production of methanol, in which at least two catalyst layers are provided. The first catalyst layer is arranged upstream and the second catalyst layer is arranged downstream. The activity of the first catalyst layer is higher than the activity of the second catalyst layer.

By arranging, according to the invention, the first layer of catalyst material with a higher activity upstream, a high conversion of synthesis gas is achieved at the beginning of the catalyst bed and correspondingly large amounts of heat are generated. Hereby, an optimal temperature for the reaction of about 250° C. is achieved. The further catalyst layer of lower activity prevents or reduces the development of a pronounced hotspot which could rapidly diminish the catalyst activity. The dimension of a developing hotspot will change, with increasing operation time, from initially acute and high to increasingly wider and flatter and additionally wandering downstream.

Preferably, the layer thickness of the first upstream catalyst layer is chosen smaller, preferably significantly smaller, than the layer thickness of the downstream layer. In that case, the upstream highly-active catalyst layer serves for heating up the catalyst bed to an optimal temperature. In the further pathway of the catalyst bed, i.e. in the area of the second downstream catalyst layer with lower activity, less amounts of heat are produced and a deactivation of the catalyst is prevented. The layer thickness of the first catalyst layer is chosen such that there is not reached a temperature in this thin layer which would enable the development of a pronounced hotspot.

In one embodiment, the catalyst layers are provided directly adjacent to each other in the flow direction of the synthesis gas. In a further embodiment, the layers are provided within a single catalyst fill in the catalyst bed. Between the catalyst layers, inert material may be arranged. Within this layer structure, the temperature can be kept within the desired limits by the layer thickness and activity of the used catalysts.

Advantageously, further catalyst layers, preferably two further catalyst layers, are provided in the reactor, wherein the catalyst layers are each arranged downstream of the second catalyst layer, and wherein the activity of the catalyst layers successively increases towards the downstream end of the reactor.

In this way, a layer arrangement of multiple, preferably four, catalyst layers is created. The activities of the single catalyst layers are chosen such that the conversion of the synthesis gas is optimized. The first layer has a relatively high activity to ensure heating up of the reactor to an optimal temperature as described above. By using a layer with high activity, a temperature of 230° C. to 260° C., preferably around 250° C., can be achieved in this layer. This catalyst layer is preferably configured significantly thinner than the further catalyst layers, since this layer is predominantly utilized for heating the reactor up. This layer is configured so thin that no pronounced hotspot is formed. Additionally, a partial conversion of the synthesis gas takes place in the first layer. In one embodiment, the different catalyst layers are arranged directly adjacent to each other in the flow direction of the synthesis gas.

The second catalyst layer has a lower activity. This layer is used to prevent a hotspot or to hinder its development as described above. This layer thus ensures that the hotspot is generated broad and flat and that no accelerated deactivation of catalyst material of high activity occurs. Preferably, catalyst material which has a high long-term stability is used for this catalyst layer. This layer can consist of partly-deactivated, reused catalyst material or of catalyst material which has inherently lower activity. The activity of a catalyst can be adapted by adding an activity-moderating promoter or selective catalyst poison or by diluting with an inert filling material. The activity indicates the degree of conversion from reactants to products per unit length of the reactor. The activity is influenced by the chemical composition, doping, poisoning, available surface etc. of the catalyst material, and also by the catalyst geometry. Exemplarily, a catalyst with high activity in the form of a large sphere has a lower activity than a catalyst with a low activity in the form of microspheres.

The following further catalyst layers have a successively rising activity, i.e. higher activities than the previously described second catalyst layer. In this way, the conversion of synthesis gas is maximized. The downstream of the second catalyst layer arranged further catalyst layers can maintain their high activity for a long time, since a partial conversion of the synthesis gas has already taken place. The partial conversion of the synthesis gas leads to the remaining synthesis gas being less reactive, since the ratio between reactants and products has shifted towards the products. The heat development is thus reduced despite the highly-active catalyst layers.

Preferably, the layer thickness of the first catalyst layer is 5% to 20%, preferably 10%, of the total thickness of all catalyst layers, and preferably the layer thickness of the further catalyst layers is 30% of the total thickness of all catalyst layers, respectively.

Preferably, all used catalysts are copper-based catalysts. Methanol synthesis catalysts of the type $Cu/Zn/Al_2O_3$ are used for the methanol synthesis with different copper dispersions and thus different activities.

Preferably, the catalyst layers have the same catalyst material, wherein the catalyst layers with lower activity comprise partially deactivated catalyst material.

Preferably, such a partially deactivated catalyst is provided by using an already employed downstream methanol synthesis catalyst which has been used for a longer time and which has thus lost a part of its activity. Preferably, the partially deactivated catalyst is removed from the downstream catalyst layer, this catalyst layer is filled with fresh, highly-active catalyst, and the previously removed, partially deactivated catalyst, is employed in the second catalyst layer with a lower activity. Where appropriate, the partially deactivated catalyst is, as known to the skilled person, inerted, exemplarily by controlled oxidation, and reactivated with reducing gases. Using this approach, exclusively fresh, highly-active catalyst is purchased, the operation time of which can be enhanced, thus leading to economic advantages and a lowering in the amount of deactivated catalyst to be disposed.

Preferably, the catalyst layers comprise different catalysts. An optimal adjustment of activity and long-term stability of the first and second catalyst layer can thus be achieved.

Preferably, the catalysts are solid. More preferably, the catalysts are provided in the form of packed bed fillings. The catalyst layers are formed by subsequently filling the desired catalyst layers in the packed bed. In this way, the catalyst layers may be arranged directly adjacent to each other. Also, inert material may be provided between the catalyst layers to prevent a mixing of the catalysts and to simplify removal of individual layers. During filling, it is ensured that the catalyst layers are arranged successively in the flow direction of the synthesis gas.

By this arrangement, the catalysts are arranged in the reactor in the desired layers. Further, the catalysts can be easily removed from the reactor layer by layer.

Preferably, the catalyst layers are formed from catalysts in the form of pellets, wherein more preferably the pellet size of the catalysts of the catalyst layers is different.

The pellet size of the catalysts influences the diffusion inhibition of the catalyst material. The smaller the used pellets are, the lower is the diffusion inhibition of the catalyst material. Reactants can diffuse faster into the pellet material and methanol can be transported faster out of the material. Smaller pellets are preferably used in highly-active downstream layers. Larger pellets are preferably used for layers which are supposed too have relatively low activity, exemplarily cylindrically-formed pellets with a diameter of 6 mm and a height of 4 mm.

Preferably, the reactor is configured as a water-cooled reactor. Alternatively, the reactor is configured as a gas-cooled reactor. The reactor can also be configured as a non-cooled, adiabatic reactor.

According to a further aspect, a method for the catalytic production of methanol from synthesis gas is proposed. The method comprises the following steps:

providing a reactor;
arranging at least two catalyst layers in the reactor, wherein the first catalyst layer is arranged upstream and the second catalyst layer is arranged downstream, and wherein the activity of the first catalyst layer is higher than the activity of the second catalyst layer;
applying synthesis gas to the reactor, comprising hydrogen and carbon oxides,
converting the synthesis gas in the reactor under methanol synthesis conditions to methanol,
channeling the produced methanol and the non-converted synthesis gas out of the reactor.

Preferably, the cooling temperature of the reactor, which is preferably configured as a water-cooled reactor, during the synthesis reaction is 200° C. to 260° C., preferably 230° C. to 250° C.

The temperature of about 230° C. to 250° C. is considered to be the optimal temperature for methanol synthesis. The upstream catalyst layer heats up the synthesis gas to the optimal reaction temperature by means of the reaction heat. Also, heating the water of the reactor to an optimal temperature can be achieved in this case. The water can subsequently be used for driving a steam turbine.

Preferably, the temperature during the synthesis reaction of the synthesis gas does not exceed 250° C. to 270° C. and preferably about 260° C. in all catalyst layers.

By adjusting the activity in subsequent catalyst layers, that is by reducing the activity in the second layer and successively raising the activity in the preferably provided subsequent layers, the temperature in the catalyst layers does not rise to high temperatures. Therefore, the deactivation of the catalysts occurs slower than at a high maximum temperature of exemplarily 280° C. At the same time, employing optimally adjusted catalyst layers leads to an enhanced volume-specific productivity of methanol (space-time-yield) of the synthesis gas.

In the method according to the invention, more than 70%, preferably more than 75%, and more preferably more than 79% of the carbon monoxide of the synthesis gas is converted in the reactor during one gas passage. This is achieved by preventing a relatively fast deactivation of catalyst material with high activity by the inventive arrangement of catalyst layers.

In the method according to the invention more than 25%, preferably more than 30%, and more preferably more than 33% of the carbon dioxide of the synthesis gas is converted in the reactor during one gas passage.

The term "upstream" and "downstream" denotes the arrangement of the catalyst layers in the reactor. In the reactor, a gas entry side and a gas exit side are provided for the synthesis gas. The synthesis gas enters through the gas entry side into the inner chamber of the reactor, in which the catalyst layers are provided. After flowing through the catalyst layers, the synthesis gas exits the reactor through the gas exit side. The flow of synthesis gas therefore defines a direction, wherein the synthesis gas enters through the "upstream" gas entry side into the inner chamber of the reactor and exits the inner chamber of the reactor through the "downstream" gas exit side. The first catalyst layer is thus arranged in the reactor closer to the gas entry side than the second catalyst layer, which is arranged closer to the gas exit side of the reactor.

The invention will be described in the following with reference to the attached figures by multiple examples in more detail. The figures show.

BASIC ARRANGEMENT

Figure 1:
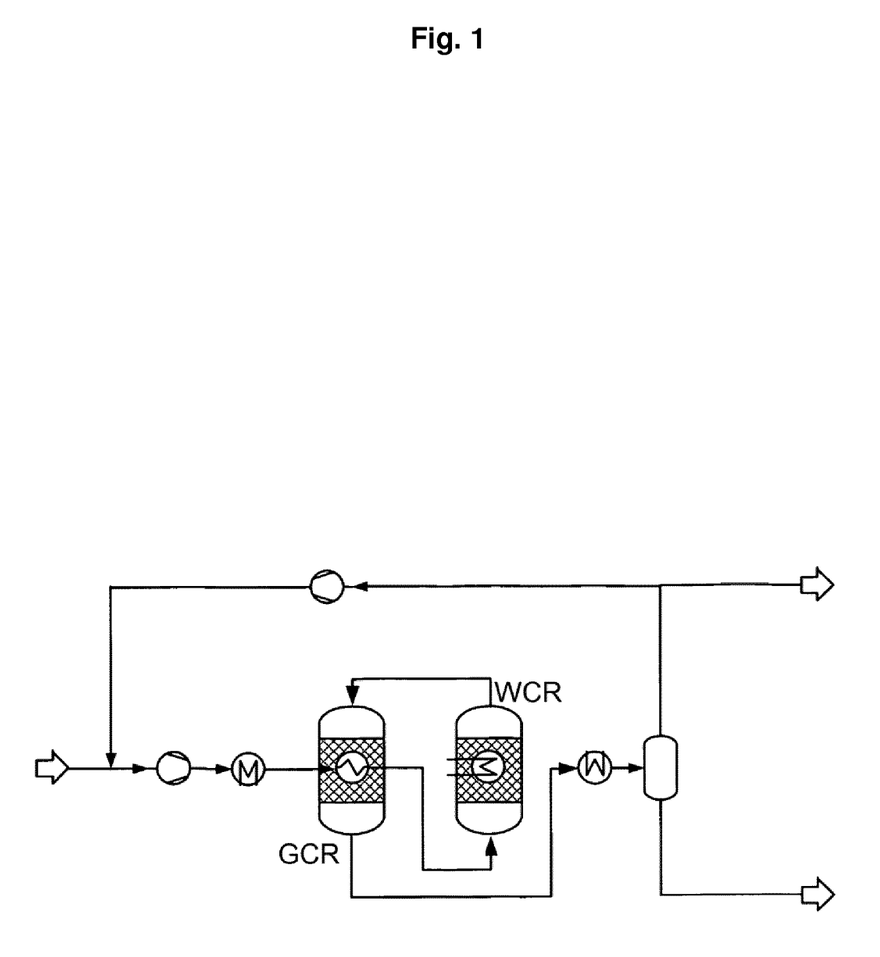
FIG. 1 a schematic depiction of an arrangement of two reactors according to the application WO 2011/101081 A1.
Figure 2:
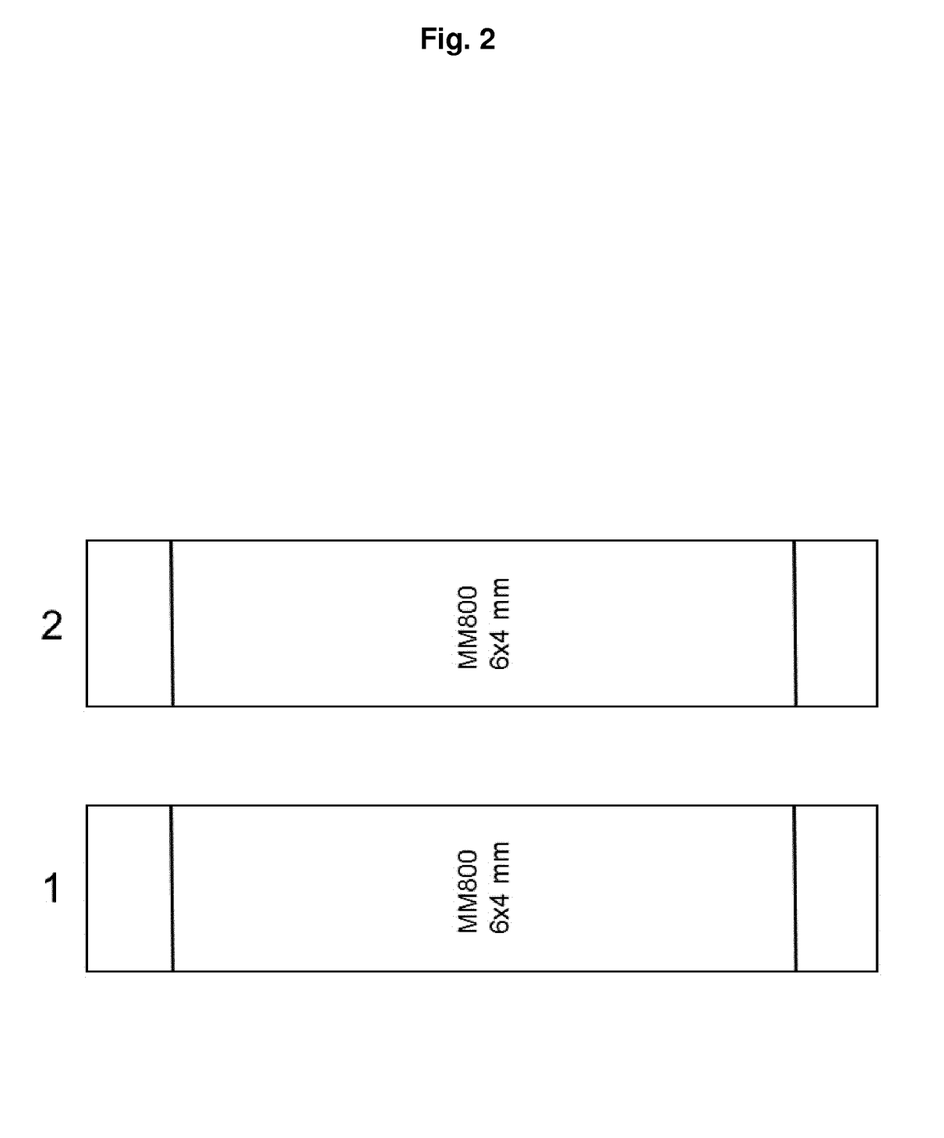
FIG. 2 a schematic basic arrangement of two reactors with one catalyst layer each.

The basic arrangement which is provided as a comparative arrangement has been chosen such that it resembles the structure of an arrangement which is typically used in the industry for a methanol synthesis plant, in which two reactors with one catalyst layer each are utilized, and as it is exemplarily described in the application WO 2011/101081 A1. For the specific description of the components which are depicted in FIG. 1, it is thus referred to the description of FIG. 1 in the application WO 2011/101081 A1. In the basic arrangement, two reactors 1 and 2 are utilized. In both reactors, the same catalyst material MegaMax® 800 with a pellet size of 6×4 mm is used. However, in this and the subsequently described examples, random catalyst materials such as copper-based methanol synthesis catalysts can be utilized, as long as the catalyst layers have the desired activity and thickness to prevent or reduce the formation of a hotspot. The first reactor, reactor 1, is configured as a water-cooled reactor (WCR—water cooled reactor), whereas the second reactor, reactor 2, is configured such that it resembles the temperature profile of a gas-cooled reactor (GCR—gas cooled reactor), which is known from the prior art. The schematic structure of the basic arrangement is depicted in FIG. 2. In the following tables, the measurement values of this basic arrangement are reproduced in the third column.

In the following tables, $m_{catalyst}$ denotes the mass of the used catalyst material. $T_{cool(first\ reactor)}$ denotes the temperature of the water mantle in the area of the first catalyst layer. The recycle ratio RR denotes the ratio between fresh and reused, non-converted synthesis gas. GHSV denotes the gas hourly space velocity. $T_{max}$ denotes the maximum temperature occurring in the catalyst layers during the synthesis reaction. $X_{CO\_pp\ (first\ reactor)}$ denotes the amount of converted carbon monoxide in the first reactor, wherein the first reactor in the examples according to the invention is the reactor in which the catalyst layers according to the invention are arranged. $X_{CO2\_pp\ (first\ reactor)}$ denotes the amount of converted carbon dioxide in the first reactor. $X_{CO\_pp\ (all\ reactors)}$ (pp—per pass) denotes the amount of converted carbon monoxide in all reactors in total. $X_{CO2\_pp\ (all\ reactors)}$ denotes the amount of converted carbon dioxide in all reactors in total. $STY_{(first\ reactor)}$ denotes the specific product outputs or space-time-yield, i.e. the quantity of product formed in the first reactor per volume and time. $STY_{(all\ reactors)}$ denotes correspondingly the specific product output of all reactors. This nomenclature applies also to the following examples according to the invention. Thus, the basic arrangement with two reactors is compared with the arrangement according to the invention of multiple catalyst layers in one reactor.

Example 1

Figure 3:
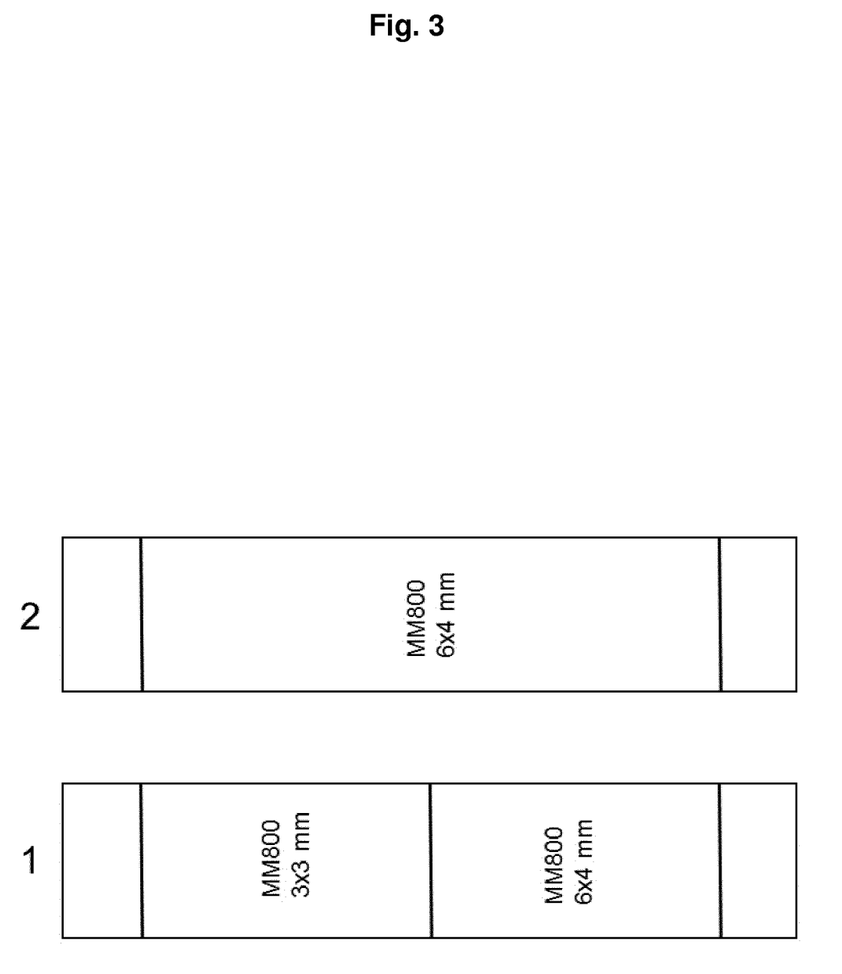
FIG. 3 an illustrative first arrangement of a reactor with two catalyst layers according to the invention.

As depicted in FIG. 3, two catalyst layers are provided in the first arrangement in reactor 1 according to the invention. The two catalysts are catalysts of the MegaMax® series, particularly MegaMax® 800 catalysts, wherein the catalysts have different pellet sizes. Other catalysts can also be utilized such as copper-based methanol synthesis catalysts. The first catalyst layer has a pellet size of 3×3 mm, wherein the second catalyst layer has a pellet size of 6×4 mm.

Synthesis gas travels from the first catalyst layer to the second catalyst layer. The first catalyst layer has a higher activity than the second catalyst layer.

Additionally, as depicted in FIG. 3, a further reactor 2 is provided, which exhibits only one catalyst layer. This reactor only contains one catalyst with moderate activity (Mega-Max® 800 with a pellet size of 6×4 mm). Apart from the provision of two catalyst layers in the water-cooled reactor 1, the structure corresponds to the structure which is depicted in FIG. 2.

In the following, a comparison of the arrangement according to the first example of the invention (second column) and the basic arrangement (third column) is depicted in tabular form.

TABLE 1

|  | 2-layer catalyst bed - 2 reactors | basic arrangement - 1 catalyst - 2 reactors | unit |
|---|---|---|---|
| $m_{catalyst}$ | 2.8 | 2.8 | Kg |
| $T_{cool\ (first\ reactor)}$ | 230 | 250 | ° C. |
| recycle ratio | 1.6 | 1.6 | — |
| GHSV | 15000 | 15000 | h$^{-1}$ |
| $T_{max}$ | 286.4 +/− 2.2 | 284.0 +/− 2.1 | ° C. |
| $X_{CO\_pp}$ (first reactor) | 87.7 +/− 1.2 | 69.8 +/− 1.2 | % |
| $X_{CO2\_pp}$ (first reactor) | 30.0 +/− 7.4 | 15.2 +/− 3.7 | % |
| $X_{CO\_pp}$ (all reactors) | 90.2 +/− 1.1 | 86.3 +/− 1.2 | % |
| $X_{CO2\_pp}$ (all reactors) | 35.0 +/− 3.4 | 25.0 +/− 6.9 | % |
| $STY_{(first\ reactor)}$ | 2.02 +/− 0.11 | 1.70 +/− 0.06 | kg/(l * h) |
| $STY_{(all\ reactors)}$ | 0.91 +/− 0.12 | 0.96 +/− 0.05 | kg/(l * h) |

This comparison shows that, by providing 2 catalyst layers in the first reactor as described above, the conversion of carbon monoxide can be increased by about 18% and the conversion of carbon dioxide of about 15%. Also, the specific product output in the first reactor can be increased by about 18%. By the enhanced conversion of carbon oxides in the first reactor, the heat production can furthermore be increased. Although the temperature of the coolant has been reduced in the example, the maximum temperature $T_{max}$ is increased in comparison to the basic arrangement. The reduced cooling temperature contributes about 8% to the increased conversion of carbon monoxide, since a higher equilibrium conversion occurs at this temperature.

Example 2

Figure 4:
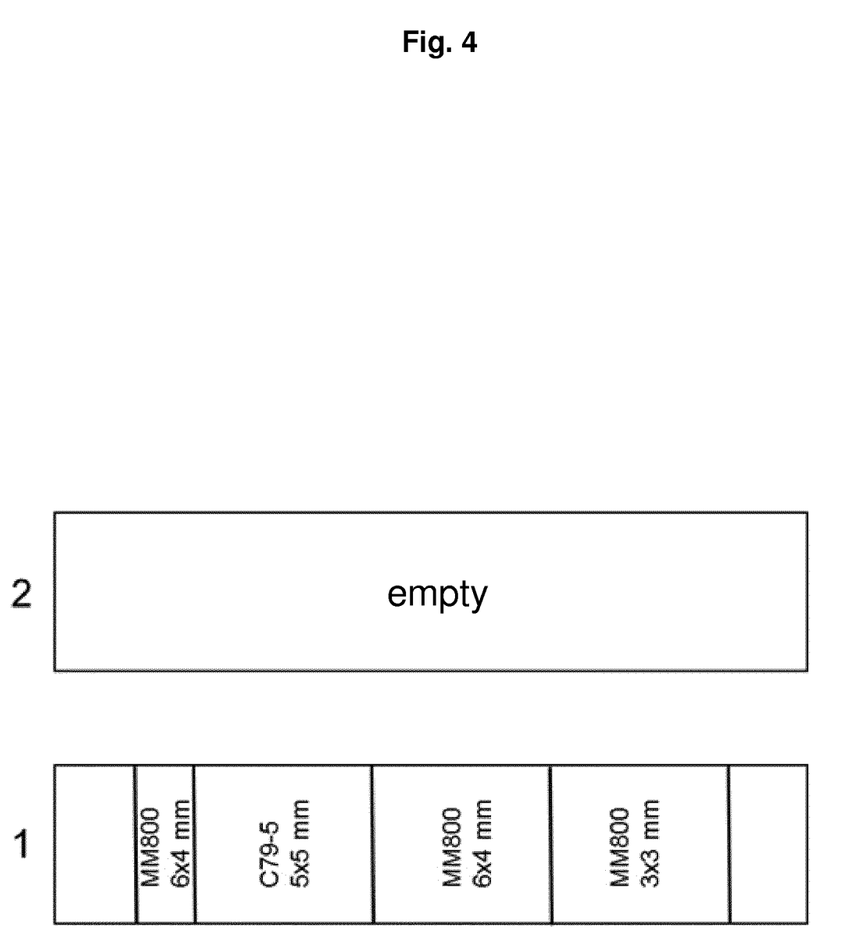
FIG. 4 an illustrative second arrangement of a reactor with four catalyst layers according to the invention.

FIG. 4 shows a second arrangement according to the invention, in which only one reactor filled with catalyst is provided. This reactor is water-cooled. The arrangement corresponds to the arrangement which is shown in FIG. 2 with the difference that, instead of the two reactors 1 and 2, only the water-cooled reactor 1 is filled with catalyst material, and reactor 2 remains empty. In this reactor 1, four catalyst layers are provided, wherein part of these catalysts are catalysts of the MegaMax® series. The layers are configured as a first layer of MegaMax® 800 with a pellet size of 6×4 mm and a relative layer thickness of 10%, in relation to the total thickness of all catalyst layers. The second layer is C79-5 with a pellet size of 5×5 mm and a relative layer thickness of 30%. The third layer is Mega-Max® 800 with a pellet size of 6×4 mm with a relative layer thickness of 30%. The fourth layer is MegaMax® 800 with a pellet size of 3×3 mm with a relative layer thickness of 30%. Also, other catalysts such as copper-based methanol synthesis catalysts can be utilized. The catalysts and pellet sizes are chosen such that the activity of the last catalyst layer is highest. The second layer has the lowest activity.

As can be seen in the following table 2, the conversion of the carbon oxides and the specific product output in the arrangement according to the invention is enhanced compared to the basic arrangement by about 10% (CO) and 18% ($CO_2$). Also, due to the increased conversion of carbon oxides, the heat generation in the reactor is increased, which leads to a higher maximum temperature $T_{max}$ in the catalyst bed. Since only one reactor is used in the arrangement according to the invention, the specific product output of the whole plant is increased by about 115%.

TABLE 2

| | 4-layer catalyst bed - 1 reactor | Basic arrangement - 1 catalyst - 2 reactors | Unit |
|---|---|---|---|
| $m_{catalyst}$ | 1.5 | 2.8 | Kg |
| $T_{cool\ (first\ reactor)}$ | 250 | 250 | ° C. |
| recycle ratio | 1.6 | 1.6 | — |
| GHSV | 15000 | 15000 | $h^{-1}$ |
| $T_{max}$ | 286.2 +/− 1.0 | 284.0 +/− 2.1 | ° C. |
| $X_{CO\_pp\ (first\ reactor)}$ | 79.7 +/− 1.0 | 69.8 +/− 1.2 | % |
| $X_{CO2\_pp\ (first\ reactor)}$ | 33.2 +/− 1.7 | 15.2 +/− 3.7 | % |
| $X_{CO\_pp\ (all\ reactors)}$ | — | 86.3 +/− 1.2 | % |
| $X_{CO2\_pp\ (all\ reactors)}$ | — | 25.0 +/− 6.9 | % |
| $STY_{(first\ reactor)}$ | 2.06 +/− 0.03 | 1.70 +/− 0.06 | kg/(l * h) |
| $STY_{(all\ reactors)}$ | — | 0.96 +/− 0.05 | kg/(l * h) |

Example 3

In the third example, a structural arrangement has been chosen, as is shown in FIG. 4. In comparison to the second example, the synthesis reaction has been conducted at a lower temperature. This leads to a lower deactivation of the catalysts and therefore to a higher yield. It is assumed that the activity of the catalysts after 1000 hours of operation is about 10% higher than the activity of the catalysts in the basic arrangement. As shown in the following table, the conversion of carbon oxides increases in comparison to the basic arrangement by about 13% (CO) and 19% ($CO_2$), and the specific product output of the reactor by 22%.

TABLE 3

| | 4-layer catalyst bed - 1 reactor | Basic arrangement - 1 catalyst - 2 reactors | Unit |
|---|---|---|---|
| $m_{catalyst}$ | 1.5 | 2.8 | Kg |
| $T_{cool\ (first\ reactor)}$ | 230 | 250 | ° C. |
| recycle ratio | 1.6 | 1.6 | — |
| GHSV | 15000 | 15000 | $h^{-1}$ |
| $T_{max}$ | 260.5 +/− 0.6 | 284.0 +/− 2.1 | ° C. |
| $X_{CO\_pp\ (first\ reactor)}$ | 82.4 +/− 0.6 | 69.8 +/− 1.2 | % |
| $X_{CO2\_pp\ (first\ reactor)}$ | 34.2 +/− 1.2 | 15.2 +/− 3.7 | % |
| $X_{CO\_pp\ (all\ reactors)}$ | — | 86.3 +/− 1.2 | % |
| $X_{CO2\_pp\ (all\ reactors)}$ | — | 25.0 +/− 6.9 | % |
| $STY_{(first\ reactor)}$ | 2.07 +/− 0.04 | 1.70 +/− 0.06 | kg/(l * h) |
| $STY_{(all\ reactors)}$ | — | 0.96 +/− 0.05 | kg/(l * h) |

Figure 5:
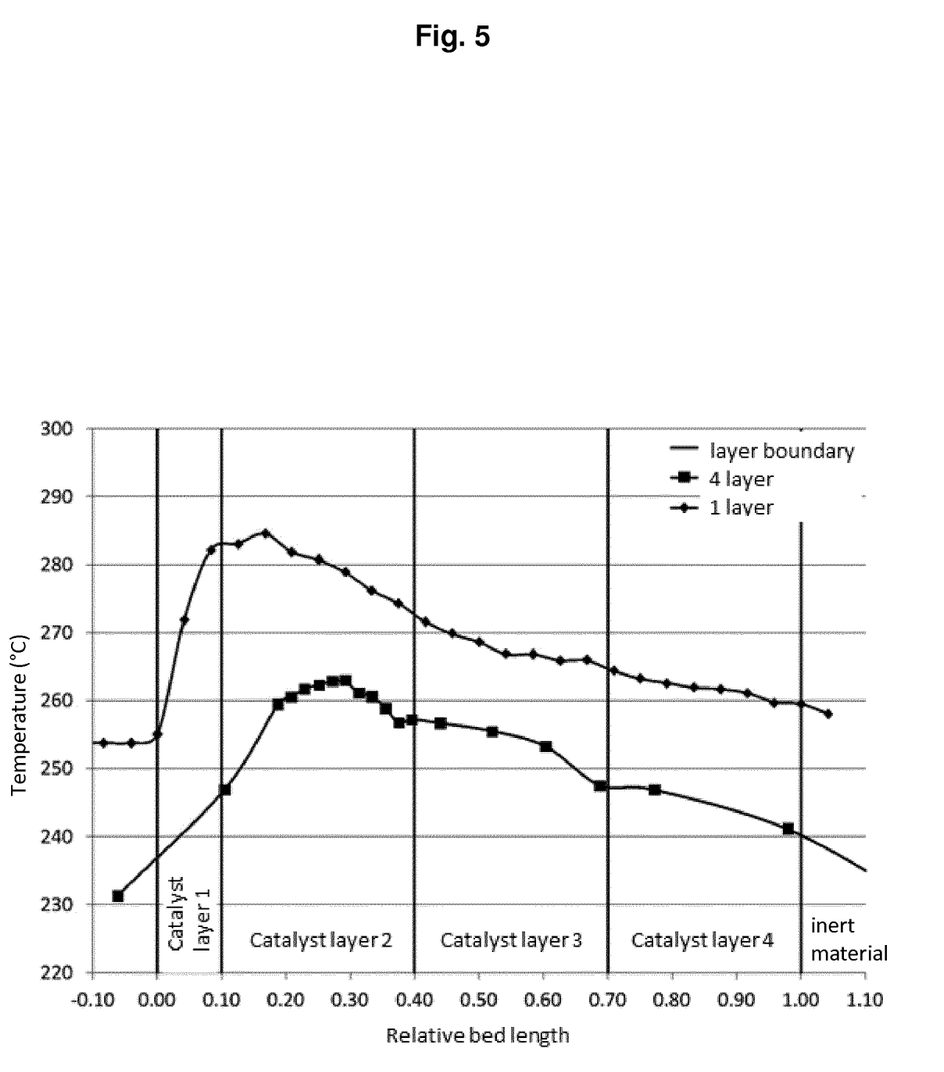
FIG. 5 an exemplarily measurement diagram for comparing the third example with the basic arrangement

FIG. 5 shows the temperature development within the catalyst layers during the synthesis reaction in the basic arrangement and in the arrangement which is shown in FIG. 4 at a lower temperature regime (example 3). By using four catalyst layers, the temperature in the catalyst layers can be reduced, while at the same time the conversion of carbon oxides and the specific product output can be enhanced.

The above described exemplary embodiments are not to be understood limiting. Other embodiments which are consistent with the above described exemplary embodiments are now sufficiently described for the skilled person.

The invention claimed is:

1. Method for the catalytic production of methanol from synthesis gas,
wherein the method comprises the following steps:
providing a reactor;
arranging at least two catalyst layers for the production of methanol in the reactor,
wherein the first catalyst layer is arranged upstream and the second catalyst layer is arranged downstream, and wherein the activity of the first catalyst layer is higher than the activity of the second catalyst layer;
applying synthesis gas to the reactor, comprising hydrogen and carbon oxides,
converting the synthesis gas in the reactor under methanol synthesis conditions to methanol,
channeling the produced methanol and the non-converted synthesis gas out of the reactor.

2. Method according to claim 1, wherein the reactor is a water-cooled reactor and the cooling temperature is between 200° C. and 260° C.

3. Method according to claim 1, wherein at least two further catalyst layers for the production of methanol from synthesis gas are arranged in the reactor, wherein the further catalyst layers are each arranged downstream of the second catalyst layer, and wherein the activity of the further catalyst layers successively increases towards the downstream end of the reactor.

4. Method according to claim 1, wherein the cooling temperature and the layer thickness and the activity of the individual catalyst layers is chosen such that the resulting reaction temperature in the reactor does not exceed about 260° C.

5. Method according to claim 2 wherein the cooling temperature is between 230° C. and 250° C.

6. Reactor for the catalytic production of methanol, comprising at least two catalyst layers for the production of methanol arranged in the reactor, wherein the first catalyst layer is arranged upstream and the second catalyst layer is arranged downstream, and wherein the activity of the first catalyst layer for the production of methanol is higher than the activity of the second catalyst layer.

7. Reactor according to claim 6, wherein the catalyst layers are arranged directly adjacent to each other.

8. Reactor according to claim 6, wherein the catalyst layers are arranged in a single packed bed filling.

9. Reactor according to claim 6, wherein the at least two catalyst layers have an essentially identical layer thickness.

10. Reactor according to claim 6, wherein further catalyst layers for the production of methanol, are arranged in the reactor, wherein the further catalyst layers are each arranged downstream of the second catalyst layer, and wherein the activity of the further catalyst layers for the production of methanol successively increases towards the downstream end of the reactor.

11. Reactor according to claim 9, wherein further catalyst layers for the production of methanol, are arranged in the reactor, wherein the further catalyst layers are each arranged downstream of the second catalyst layer, and wherein the activity of the further catalyst layers for the production of methanol successively increases towards the downstream end of the reactor.

12. Reactor according to claim 10, wherein the layer thickness of the first catalyst layer is smaller than the layer thickness of the further catalyst layers.

13. Reactor according to claim 12, wherein the layer thickness of the first catalyst layer is 5% to 20% and wherein the further catalyst layers exhibit a substantially identical layer thickness.

14. Reactor according to claim 13, wherein a total of four catalyst layers are provided, wherein the layer thickness of the first catalyst layer is 10% of the total thickness of all catalyst layers, and wherein the layer thickness of the three further catalyst layers each is about 30% of the total thickness of all catalyst layers.

15. Reactor according to claim 10 wherein two further catalyst layers for the production of methanol are provided.

16. Reactor according to claim 11 wherein two further catalyst layers for the production of methanol are provided.

17. Reactor according to claim 12 wherein the layer thickness of the first catalyst layer is 10% of the total thickness of all catalyst layers.

\* \* \* \* \*